United States Patent
Veiby

(10) Patent No.: US 10,335,494 B2
(45) Date of Patent: Jul. 2, 2019

(54) COMBINATION OF AURORA KINASE INHIBITORS AND ANTI-CD30 ANTIBODIES

(71) Applicant: Millennium Pharmaceuticals, Inc., Cambridge, MA (US)

(72) Inventor: Ole Petter Veiby, Westborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/101,952

(22) PCT Filed: Dec. 8, 2014

(86) PCT No.: PCT/US2014/069005
§ 371 (c)(1),
(2) Date: Jun. 6, 2016

(87) PCT Pub. No.: WO2015/085289
PCT Pub. Date: Jun. 11, 2015

(65) Prior Publication Data
US 2016/0303249 A1 Oct. 20, 2016

Related U.S. Application Data

(60) Provisional application No. 61/912,785, filed on Dec. 6, 2013.

(51) Int. Cl.
*A61K 31/55* (2006.01)
*A61K 45/06* (2006.01)
*A61K 47/68* (2017.01)

(52) U.S. Cl.
CPC ......... *A61K 47/6803* (2017.08); *A61K 31/55* (2013.01); *A61K 45/06* (2013.01); *A61K 47/6849* (2017.08); *A61K 47/6867* (2017.08)

(58) Field of Classification Search
None
See application file for complete search history.

(56) References Cited

U.S. PATENT DOCUMENTS 7,790,160 B2 * 9/2010 Von Strandmann ............ A61K 39/39541
424/130.1
2013/0004481 A1 1/2013 Solca et al.

FOREIGN PATENT DOCUMENTS

WO WO 2004/010957 A2 2/2004
WO WO 2010/074724 A1 7/2010
WO WO 2010/081004 A1 7/2010

OTHER PUBLICATIONS

Manfredi et al.—Characterization of Alisertib (MLN8237), an investigational small-molecule inhibitor of Aurora A kinase using novel in vivo pharmacodynamic assays. Clin. Cancer Res. 17, 7614-7624, 2011.*
Jagadeesh et al. Novel targeted therapies in peripheral T cell lymphoma. Discovery Medicine, 15, 367-378, 2013.*
European Patent Application No. 14867637.2, by Millenium Pharmaceuticals, Inc.: Supplementary European Search Report and European Search Opinion, dated Aug. 17, 2017 (9 pages).
International Patent Application No. PCT/US2014/069005, filed Dec. 8, 2014, by Millenium Pharmaceuticals, Inc., International Search Report and Written Opinion, dated Mar. 6, 2015 (11 pages).
Jagadeesh et al., (2013) "Novel targeted therapies in peripheral T cell lymphoma" *Discovery Medicine* 15(85):367-378.
Oflazoglu et al., (2008) "Combination of the anti-CD30-auristatin-E antibody drug conjugate (SGN-35) with chemotherapy improves antitumor activity in Hodgkin lymphoma" *British Journal of Haematology* 142(1):69-73.
Friedberg et al., (2011) "Phase 2 Trial of Alisertib (MLN8237), an Investigational, Potent Inhibitor of Aurora A Kinase (AAK), in Patients (pts) with Aggressive B- and T-Cell Non-Hodgkin Lymphoma (NHL)", *Blood*, 118(21):95.
O'Connor et al., (2015) "First Multicenter, Randomized Phase 3 Study in Patients (Pts) with Relapsed/Refractory (R/R) Peripheral T-Cell Lymphoma (PTCL): Alisertib (MLN8237) Versus Investigator's Choice (Lumiere trial; NCT01482962)", *Blood*, 126(23):341.
Pro et al., (2012) "Brentuximab vedotin (SGN-35) in patients with relapsed or refractory systemic anaplastic large-cell lymphoma: results of a phase II study", *J. Clin. Oncol.*, 30(18):2190-2196.
Oki et al., (2012) "Brentuximab vedotin in systemic T-cell lymphoma", *Expert Opin. Biol. Ther.*, 12(5):623-632.
Qi et al., (2013) "Alisertib (MLN8237) an investigational agent suppresses Aurora A and B activity, inhibits proliferation, promotes endo-reduplication and induces apoptosis in T-NHL cell lines supporting its importance in PTCL treatment", *Leukemia Research*, 37(4):434-439.

* cited by examiner

*Primary Examiner* — Elly-Gerald Stoica
(74) *Attorney, Agent, or Firm* — Finnegan, Henderson, Farabow, Garrett and Dunner LLP

(57) ABSTRACT

The present invention relates to methods for the treatment of cancers. In particular, the invention provides methods for treatment of cancer by administering an Aurora kinase inhibitor in combination with an anti-CD30 antibody. The combined administration of the Aurora kinase inhibitor and anti-CD30 antibody can be simultaneous, separate, sequential or consecutive.

11 Claims, 2 Drawing Sheets

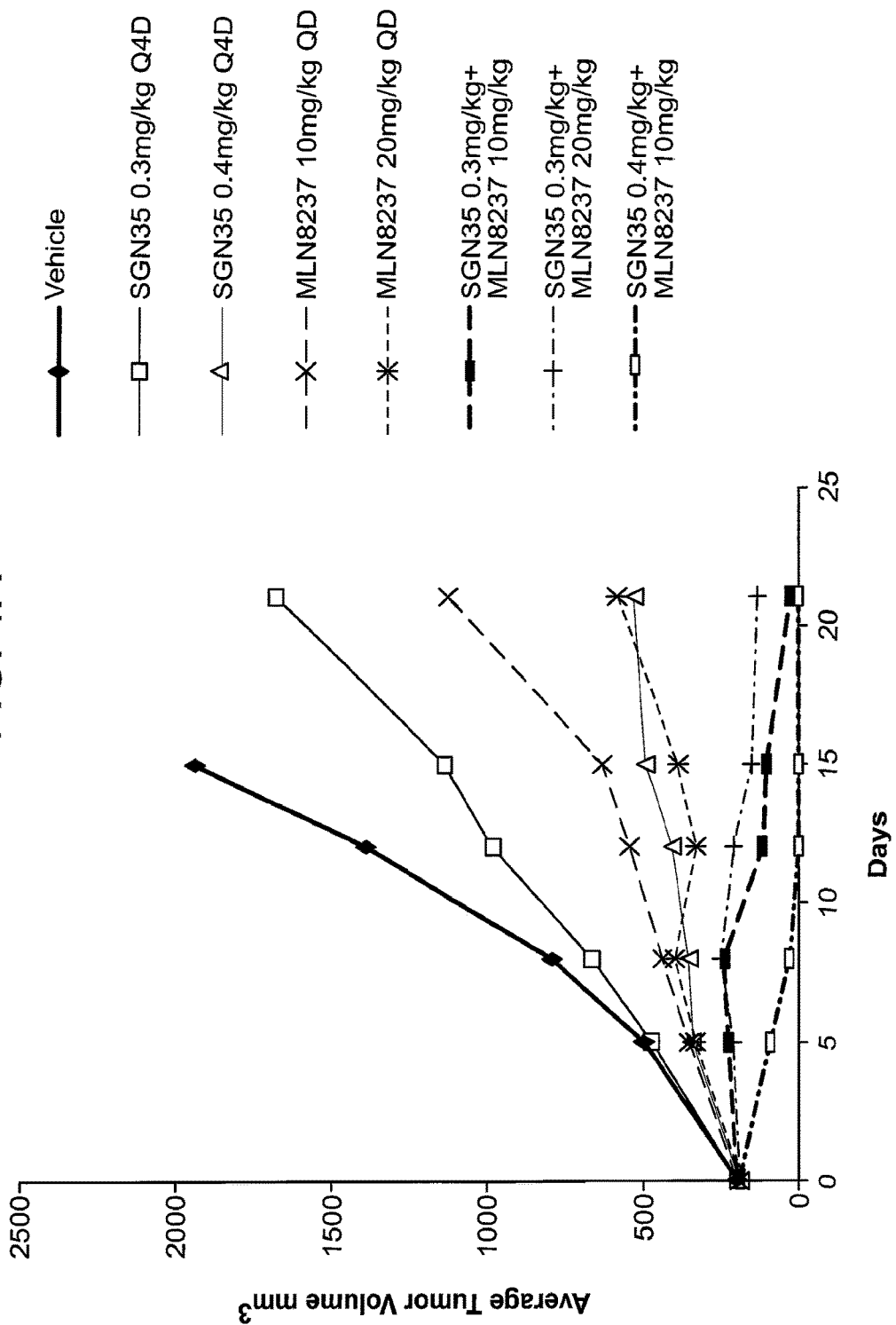

COMBINATION OF AURORA KINASE INHIBITORS AND ANTI-CD30 ANTIBODIES

REFERENCE TO RELATED APPLICATIONS

This non-provisional application claims the benefit of and priority to U.S. Provisional Application No. 61/912,785, filed Dec. 6, 2013, the contents of which are hereby incorporated by reference in its entirety.

FIELD OF THE INVENTION

This invention relates to methods for the treatment of cancer. In particular, the invention provides methods for treatment of solid tumors and hematological malignancies by administering Aurora kinase inhibitors in combination with anti-CD30 antibodies.

BACKGROUND

In 2008, there were an estimated 12.7 million cases of cancer diagnosed worldwide and about 7.6 million deaths. The global cancer burden is growing at an alarming pace; in 2030 alone, about 21.3 million new cancer cases and 13.1 million cancer deaths are expected to occur, simply due to the growth and aging of the population. Cancer is the second most common cause of death in the US, exceeded only by heart disease, accounting for nearly 1 of every 4 deaths. The National Cancer Institute estimates that approximately 13.7 million Americans with a history of cancer were alive on Jan. 1, 2012. Some of these individuals were cancer free, while others still had evidence of cancer and may have been undergoing treatment. About 1,660,290 new cancer cases are expected to be diagnosed in the US in 2013. In 2013, about 580,350 Americans are expected to die of cancer, almost 1,600 people per day. Although medical advances have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B) regulate mitotic progression through modulation of centrosome separation, spindle dynamics, spindle assembly checkpoint, chromosome alignment/segregation, and cytokinesis (Dutertre et al., *Oncogene*, 21: 6175 (2002); Berdnik et al., *Curr. Biol.*, 12: 640 (2002)). Overexpression and/or amplification of Aurora kinases have been linked to oncogenesis in several tumor types including those of colon and breast (Warner et al., *Mol. Cancer Ther.*, 2: 589 (2003); Bischoff et al., *EMBO*, 17: 3062 (1998); Sen et al., *Cancer Res.*, 94: 1320 (2002)). Moreover, Aurora kinase inhibition in tumor cells results in mitotic arrest and apoptosis, suggesting that these kinases are important targets for cancer therapy (Manfredi et al., *PNAS*, 104: 4106 (2007); Ditchfield, *J. Cell Biol.*, 161: 267 (2003); Harrington et al., *Nature Med.*, 1 (2004)). Given the central role of mitosis in the progression of virtually all malignancies, inhibitors of the Aurora kinases are expected to have application across a broad range of human tumors.

CD30, also known as TNFRSF8, is a cell membrane protein of the tumor necrosis factor receptor family and tumor marker. This receptor is expressed by activated, but not by resting, T and B cells. It is a positive regulator of apoptosis, and also has been shown to limit the proliferative potential of autoreactive CD8 effector T cells and protect the body against autoimmunity CD30 is associated with various lymphomas. CD30 is associated with anaplastic large cell lymphoma. CD30 is also expressed on classical Hodgkin Lymphoma Reed-Sternberg cells. The U.S. Food and Drug Administration has approved the therapeutic use of a CD30-directed antibody-drug conjugate (ADC), brentuximab vedotin (ADCETRIS®), for the treatment of patients with Hodgkin lymphoma after failure of autologous stem cell transplant (ASCT) or after failure of at least two prior multi-agent chemotherapy regimens in patients who are not ASCT candidates and for the treatment of patients with systemic anaplastic large cell lymphoma after failure of at least one prior multi-agent chemotherapy regimen. The European Medicines Agency has also conditionally approved brentuximab vedotin (ADCETRIS®) for i) the treatment of adult patients with relapsed or refractory CD30+ Hodgkin lymphoma following autologous stem cell transplant (ASCT) or following at least two prior therapies when ASCT or multi-agent chemotherapy is not a treatment option and ii) the treatment of adult patients with relapsed or refractory systemic anaplastic large cell lymphoma (sALCL). The anti-tumor activity of brentuximab vedotin is due to the binding of the ADC to CD30-expressing cells, followed by internalization of the ADC-CD30 complex, and the release of the conjugated payload, namely monomethyl auristatin E (MMAE) via proteolytic cleavage However, while anti-CD30 antibodies and, in particular, brentuximab vedotin, have been reported to be effective for treatment of lymphomas, such as non-Hodgkin's lymphoma, the treated patients may be subject to disease relapse. Therefore, it would be beneficial if alternative treatment regimens could be developed. Combined treatment regimens could be helpful for patients suffering from solid tumors or hematological malignancies, and might potentially even decrease the rate of relapse or overcome the resistance to a particular anticancer agent sometime seen in these patients. Additionally, combinations of anticancer agents may have additive, or even synergistic, therapeutic effects.

There is thus a need for new cancer treatment regimens, including combination therapies.

SUMMARY

The present invention provides, in part, a method of treating a patient suffering from cancer by administering to the subject a therapeutically effective amount of an Aurora kinase inhibitor in combination with a therapeutically effective amount of an anti-CD30 antibody. The combined administration of the Aurora kinase inhibitor and anti-CD30 antibody can be simultaneous, separate, sequential or consecutive. In one particular embodiment, the anti-CD30 antibody is a CD30-directed antibody-drug conjugate. In one particular embodiment, the Aurora kinase inhibitor is an Aurora A kinase inhibitor.

In one embodiment, the present invention provides for an Aurora kinase A inhibitor for use in a method for treating cancer by administration simultaneously, separately, consecutively or sequentially with an anti-CD30 antibody-drug conjugate. In one embodiment, the invention provides for an anti-CD30 antibody-drug conjugate for use in a method of treating cancer by administration simultaneously, separately, consecutively or sequentially with an Aurora A kinase inhibitor. In one embodiment, the present invention provides for an Aurora A kinase inhibitor for use in the manufacture of a medicament for treating cancer wherein the Aurora A kinase inhibitor is administered simultaneously, separately, consecutively or sequentially with an anti-CD30 antibody-drug conjugate. In one embodiment, the present invention provides for an anti-CD30 antibody-drug conjugate for use in the manufacture of a medicament for treating cancer wherein the antibody-drug conjugate is administered simultaneously, separately, consecutively or sequentially with an Aurora A kinase inhibitor.

In some embodiments, the cancer is a hematological malignancy. In some embodiments, the hematological malignancy is a lymphoma. In some embodiments the lymphoma is Hodgkin lymphoma. In some embodiments, the lymphoma is diffuse large B-cell lymphoma. In some embodiments, the lymphoma is anaplastic large cell lymphoma. In some embodiments, the lymphoma is peripheral T-cell lymphoma. In some embodiments, the lymphoma is classified as being CD30-negative. In some embodiments, the lymphoma is classified as being CD30-positive. In some embodiments the lymphoma is CD30-positive Hodgkin lymphoma. In some embodiments, the lymphoma is CD30 positive diffuse large B-cell lymphoma. In some embodiments, the lymphoma is CD30-positive anaplastic large cell lymphoma. In some embodiments, the lymphoma is CD30-positive peripheral T-cell lymphoma.

In certain embodiments, the Aurora A kinase inhibitor is 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof.

In certain embodiments, the anti-CD30 antibody-drug conjugate is an anti-CD30 antibody conjugated to an auristatin compound. Examples of auristatin compounds suitable for use in an anti-CD30 antibody-drug conjugate include, but are not limited to, MMAE or MMAF. In a particular embodiment, the anti-CD30 antibody-drug conjugate is brentuximab vedotin.

In some embodiments, the present invention provides a method of treating a patient suffering from a lymphoma (e.g., Hodgkin lymphoma, diffuse large B-cell lymphoma, peripheral T-cell lymphoma, and anaplastic large cell lymphoma), comprising administering to the subject a therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof simultaneously, separately, sequentially or consecutively with brentuximab vedotin.

In some embodiments, the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 30 mg to about 50 mg given twice daily.

In some embodiments, the therapeutically effective amount of brentuximab vedotin is about 1.0 mg/kg to 2.0 mg/kg of the patient's body weight per dose.

In one embodiment, 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered on each of days 1-7 of a 21-day cycle and bretuximab vedotin is administered on day 1 of a 21-day cycle.

In another embodiment, 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered on each of days 1-3 and 8-10 of a 21-day cycle and bretuximab vedotin is administered on day 1 of a 21-day cycle.

In yet another embodiment, 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered on each of days 1-3, 8-10 and 15-17 of a 28-day cycle and bretuximab vedotin is administered on day 1 of a 21-day cycle.

In yet another embodiment, 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered on each of days 1-3, 8-10 and 15-17 of a 28-day cycle and bretuximab vedotin is administered on day 1 of a 28-day cycle.

The disclosure contemplates all combinations of any one or more of the foregoing aspects and/or embodiments, as well as combinations with any one or more of the embodiments set forth in the detailed description and examples.

All publications, patent applications, patents and other references mentioned herein are incorporated by references in their entirety.

Other features, objects, and advantages of the invention(s) disclosed herein will be apparent from the description and drawings, and from the claims.

BRIEF DESCRIPTION OF THE DRAWINGS

FIG. 1A: Antitumor activity of brentuximab vedotin alone or in combination with MLN8237 in the SR786 xenograft ALCL model. SR786 tumor cells were injected into the subcutaneous space in the right dorsal flank of CB17 SCID F mice. Groups of mice (7 per group) were untreated or received 0.3 mg·kg or 0.4 mg/kg of brentuximab vedotin as a single agent or in combination with 10 mg/kg or 20 mg/kg of MLN8237 when the tumor size reached 200 mm$^3$. FIG. 1A demonstrates the results after the inhibition had been evaluated for a duration of 21 days.

FIG. 1B demonstrates the results of the same experiment described in FIG. 1A above, after the inhibition had been evaluated for a duration of 124 days.

DETAILED DESCRIPTION

Figure 1B:
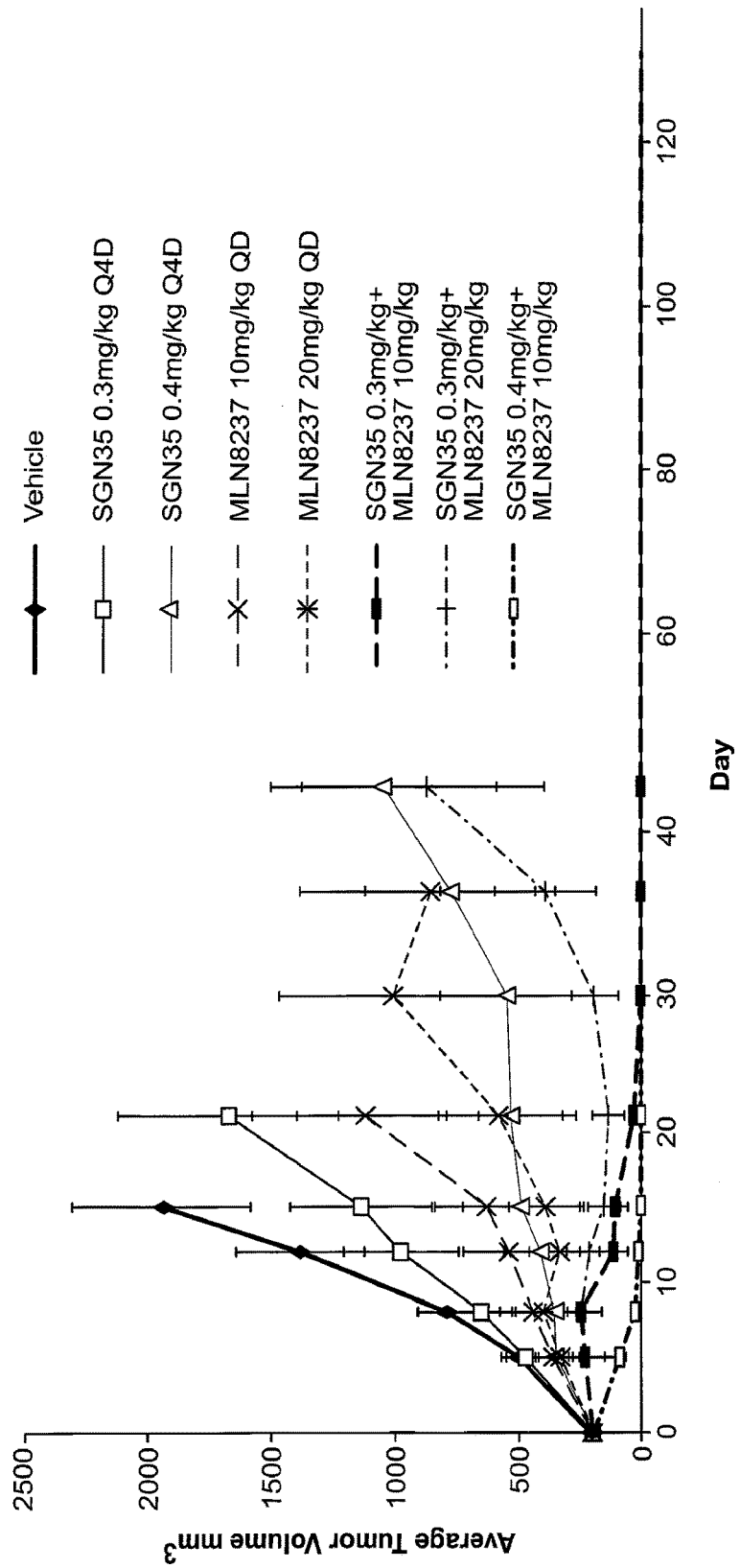
FIG. 1B: Antitumor activity of brentuximab vedotin alone or in combination with MLN8237 in the SR786 xenograft ALCL model. SR786 tumor cells were injected into the subcutaneous space in the right dorsal flank of CB17 SCID F mice. Groups of mice (7 per group) were untreated or received 0.3 mg·kg or 0.4 mg/kg of brentuximab vedotin as a single agent or in combination with 10 mg/kg or 20 mg/kg of MLN8237 when the tumor size reached 200 mm$^3$.

The present invention provides new combination therapies for the treatment of cancers. In particular, the present invention provides a method to treat a patient suffering from a cancer comprising administering to said patient a therapeutically effective amount of a Aurora kinase inhibitor simultaneously, separately, sequentially or consecutively with (e.g., before or after) an anti-CD30 antibody.

Terms used herein shall be accorded the following defined meanings, unless otherwise indicated.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound which is capable of interacting with an Aurora kinase and inhibiting its enzymatic activity. Inhibiting Aurora kinase enzymatic activity means reducing the ability of an Aurora kinase to phosphorylate a substrate peptide or protein. In some embodiments, such reduction of Aurora kinase activity is at least about 50%, at least about 75%, at least about 90%, at least about 95%, or at least about 99%. In some embodiments, the concentration of Aurora kinase inhibitor required to reduce an Aurora kinase enzymatic activity is less than about 1 µM, less than about 500 nM, less than about 100 nM, or less than about 50 nM.

In some embodiments, such inhibition is selective, i.e., the Aurora kinase inhibitor reduces the ability of an Aurora kinase to phosphorylate a substrate peptide or protein at a concentration that is lower than the concentration of the inhibitor that is required to produce another, unrelated biological effect, e.g., reduction of the enzymatic activity of a different kinase. In some embodiments, the Aurora kinase inhibitor also reduces the enzymatic activity of another kinase, preferably one that is implicated in cancer.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The terms "specific binding" and "specifically binds" mean that the anti-CD30 antibody will react, in a highly selective manner, with its corresponding target, CD30 and not with the multitude of other antigens. Typically, the anti-CD30 antibody binds with an affinity of at least about $1\times10^{-7}$ M, and preferably $10^{-8}$ M to $10^{-9}$ M, $10^{-10}$ M, $10^{-11}$ M, or $10^{-12}$ M.

As used herein, the term "comprises" means "includes, but is not limited to."

CD30 is a transmembrane glycoprotein with a molecular weight of 120 kDa. It is a member of the tumor necrosis factor receptor (TNFR) superfamily. An 85-kDa proteolytic fragment defined as soluble CD30 (sCD30) can be detected in the sera of patients with CD30-positive lymphomas and is also found in some patients with bone cancer, rheumatoid arthritis, atopic dermatitis and other reactive disorders, particularly during the acute phase of the disease. Other names for CD30 in the literature include Ki-1, Ki-1 antigen, TNFRSF8 (tumor necrosis factor receptor superfamily member 8), D1S166E (gene: CD30 is the protein encoded by this gene).

The term "antibody" as used herein refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD30), or (b) conservatively substituted derivatives of such immunoglobulin polypeptides or fragments that immunospecifically bind to the antigen (e.g., CD30). Antibodies are generally described in, for example, Harlow & Lane, *Antibodies: A Laboratory Manual* (Cold Spring Harbor Laboratory Press, 1988). As used herein, the term "antibody" includes antibodies that have been modified by covalent attachment of a heterologous molecule such as, e.g., by attachment of a heterologous polypeptide, or by glycosylation, acetylation or phosphorylation not normally associated with the antibody, and the like.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al, J. MoL Biol., 222:581-597 (1991), for example. The monoclonal antibodies herein specifically include but are not limited to "chimeric", "human" or "humanized" forms.

The antibody-drug conjugate compound for use in the present invention comprises an anti-CD30 antibody, i.e., an antibody that specifically binds to CD30, linked to a drug moiety. The drug moiety is of the auristatin type, which has been shown to interfere with microtubule dynamics and nuclear and cellular division and have anticancer activity. Auristatins of the present invention bind to tubulin and exert a cytotoxic or cytostatic effect on a Hodgkin lymphoma (HL) cell line, e.g., L540cy cell line. In some embodiments of the present invention, the auristatin drug is conjugated to the anti-CD30 antibody via a linker that is cleavable under intracellular conditions, such that cleavage of the linker releases the auristatin compound from the antibody in the intracellular environment. In yet other embodiments, the linker unit is not cleavable and the drug is released by antibody degradation.

In some embodiments, the antibody-drug conjugate compound for use in the present invention comprises an anti-CD30 antibody, i.e., an antibody that specifically binds to CD30, linked to a drug moiety, wherein the drug moiety is monomethyl auristatin E (MMAE). In some other embodiments, the antibody-drug conjugate compound for use in the present invention comprises an anti-CD30 antibody, i.e., an antibody that specifically binds to CD30, linked to a drug moiety, wherein the drug moiety is dovaline-valine-dolaisoleunine-dolaproine-phenylalanine (MMAF).

As used herein, the terms "treatment" or "treat" refer to slowing, stopping, or reversing the progression of a disease or condition in a subject, as evidenced by a decrease or elimination of a clinical or diagnostic symptom of the disease or condition. Treatment can include, for example, a decrease in the severity of a symptom, the number of symptoms, or frequency of relapse, e.g., the inhibition of tumor growth, the arrest of tumor growth, or the regression of already existing tumors.

The term "therapeutically effective amount" as used herein to refer to combination therapy means the amount of the combination of agents taken together so that the combined effect elicits the desired biological or medicinal response, i.e., inhibits the occurrence or ameliorate one or more clinical or diagnostic symptoms of lymphoma disease or condition. For example, the "therapeutically effective amount" as used herein to refer to combination therapy would be the amount of the antibody-drug conjugate compound and the amount of the Aurora kinase inhibitor that when administered together, either sequentially or simultaneously, on the same or different days during a treatment cycle, have a combined effect that is therapeutically effective and synergistic and/or provides a combination benefit. Further, it will be recognized by one skilled in the art that in the case of combination therapy with a therapeutically effective amount, as in the example above, the amount of the antibody-drug conjugate compound and/or the amount of the Aurora kinase inhibitor individually may or may not be therapeutically effective.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

The term "patient", as used herein, means an animal, preferably a mammal, more preferably a human. In some embodiments, the patient has been treated with an agent, e.g., an Aurora kinase inhibitor or an anti-CD30 antibody, prior to initiation of treatment according to the method of the invention. In some embodiments, the patient is a patient at risk of developing or experiencing a recurrence of a cancer.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It will be apparent to one skilled in the art that certain compounds described herein may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Compounds capable of inhibiting the enzymatic activity of an Aurora kinase may be used in the methods of the instant invention. In particular, Aurora kinase inhibitors include the compounds described herein, as well as compounds disclosed in, for example, WO 05/111039, US2005/0256102, US2007/0185087, WO 08/021038, US2008/0045501, WO 08/063525, US2008/0167292, WO 07/113212, EP1644376, US2005/0032839, WO 05/005427, WO 06/070192, WO 06/070198, WO 06/070202, WO 06/070195, WO 06/003440, WO 05/002576, WO 05/002552, WO 04/071507, WO 04/058781, WO 06/055528, WO 06/055561, WO 05/118544, WO 05/013996, WO 06/036266, US2006/0160874, US2007/0142368, WO 04/043953, WO 07/132220, WO 07/132221, WO 07/132228, WO 04/00833 and WO 07/056164. Also suitable for use in the methods of the invention are solvated and hydrated forms of any of these compounds. Also suitable for use in the methods of the invention are pharmaceutically acceptable salts of any of the compounds, and solvated and hydrated forms of such salts. These Aurora kinase inhibitors can be prepared in a number of ways well known to one skilled in the art of organic synthesis, including, but not limited to, the methods of synthesis described in detail in the above references.

In some embodiments the selective Aurora A kinase inhibitor is a small molecular weight compound. In particular, selective inhibitors of Aurora A kinase include the compounds described herein, as well as compounds disclosed in, for example, US Publication No. 2008/0045501, U.S. Pat. No. 7,572,784, WO 05/111039, WO 08/021038, U.S. Pat. No. 7,718,648, WO 08/063525, US Publication No. 2008/0167292, U.S. Pat. No. 8,026,246, WO 10/134965, US Publication No. 2010/0310651, WO 11/014248, US Publication No. 2011/0039826, and US Publication No. 2011/0245234, each of which is hereby incorporated by reference in its entirety, sodium 4-{[9-chloro-7-(2-fluoro-6-methoxyphenyl)-5H-pyrimido[5,4-d][2]benzazepin-2-yl]amino}-2-methoxybenzoate, KW-2449 (Kyowa), ENMD-2076 (EntreMed), and MK-5108 (Vertex/Merck).

Aurora A kinase inhibitors can be assayed in vitro or in vivo for their ability to selectively bind to and/or inhibit an Aurora A kinase. In vitro assays include assays to determine selective inhibition of the ability of an Aurora A kinase to phosphorylate a substrate protein or peptide. Alternate in vitro assays quantitate the ability of the compound to selectively bind to an Aurora A kinase. Selective inhibitor binding may be measured by radiolabelling the inhibitor prior to binding, isolating the inhibitor/Aurora A kinase complex and determining the amount of radiolabel bound. Alternatively, selective inhibitor binding may be determined by running a competition experiment in which new inhibitors are incubated with Aurora A kinase bound to a known radioligand. The compounds also can be assayed for their ability to affect cellular or physiological functions mediated by Aurora A kinase activity. In order to assess selectivity for Aurora A kinase over Aurora B kinase, inhibitors can also be assayed in vitro and in vivo for their ability to selectively bind to and/or inhibit an Aurora B kinase, using assays analogous to those described above for Aurora A kinase. Inhibitors can be assayed in vitro and in vivo for their ability to inhibit Aurora A kinase in the absence of Aurora B kinase inhibition, by immunofluorescent detection of pHisH3. (Proc. Natl. Acad. Sci. (2007) 104, 4106). Assays for each of these activities are known in the art.

In some embodiments, the Aurora A kinase inhibitor is 4-{[9-chloro-7-(2-fluoro-6-methoxyphenyl)-5H-pyrimido[5,4-d][2]benzazepin-2-yl]amino}-2-methoxybenzoic acid ((alisertib (MLN8237)) of formula (I), or a pharmaceutically acceptable salt thereof:

(I)

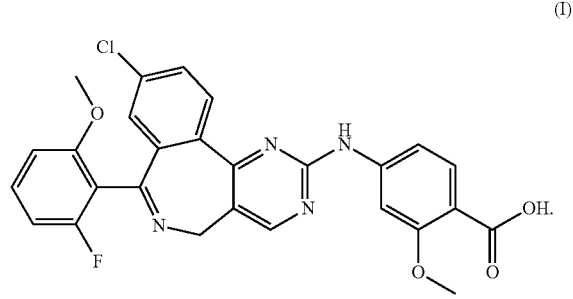 [SMILES: COc1cc(Nc2ncc3c(n2)-c2ccc(Cl)cc2C(c2c(F)cccc2OC)=NC3)ccc1C(=O)O]

In some embodiments, a pharmaceutically acceptable salt of formula (I) is sodium 4-{[9-chloro-7-(2-fluoro-6-methoxyphenyl)-5H-pyrimido[5,4-d][2]benzazepin-2-yl]amino}-2-methoxybenzoate of formula (II), or a crystalline form thereof:

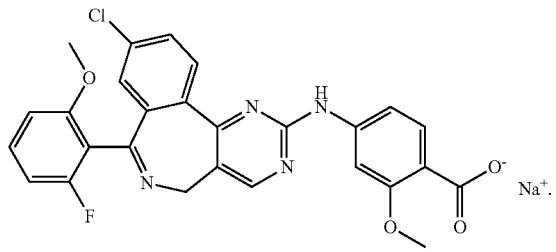

(II)

In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate. In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate monohydrate. In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate polymorph Form 2, as described in US Publication No. 2008/0167292, U.S. Pat. No. 8,026,246, and US Publication No. 2011/0245234, each of which is hereby incorporated by reference in their entirety.

The methods described herein encompass the use of an antibody-drug conjugate compound in combination therapy for the treatment of cancer. The antibody-drug conjugate compound for use in the present invention comprises an anti-CD30 antibody, i.e., an antibody that specifically binds to CD30, linked to a drug moiety. The drug moiety is of the auristatin type, which has been shown to interfere with microtubule dynamics and nuclear and cellular division and have anticancer activity. Auristatins of the present invention bind to tubulin and exert a cytotoxic or cytostatic effect on a HL cell line, e.g., L540cy cell line. In some embodiments of the present invention, the auristatin drug is conjugated to the anti-CD30 antibody via a linker that is cleavable under intracellular conditions, such that cleavage of the linker releases the auristatin compound from the antibody in the intracellular environment. In yet other embodiments, the linker unit is not cleavable and the drug is released by antibody degradation.

There are a number of different assays that can be used for determining whether an auristatin or resultant antibody-drug conjugate exerts a cytostatic or cytotoxic effect on, for example, a Hodgkin lymphoma (HL) cell line. In one example for determining whether an auristatin or resultant antibody-drug conjugate exerts a cytostatic or cytotoxic effect on a HL cell line, a thymidine incorporation assay is used. For example, HL cells at a density of 5,000 cells/well of a 96-well plated is cultured for a 72-hour period and exposed to 0.5 µCi of $^3$H-thymidine during the final 8 hours of the 72-hour period, and the incorporation of $^3$H-thymidine into cells of the culture is measured in the presence and absence of the auristatin or antibody-drug conjugate. The auristatin or resultant antibody-drug conjugate has a cytostatic or cytotoxic effect on the HL cell line if the cells of the culture have reduced $^3$H-thymidine incorporation compared to cells of the same cell line cultured under the same conditions but not contacted with the auristatin or antibody-drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on, for example HL cells indicates that an auristatin or antibody-drug conjugate is useful in the treatment or prevention of for example HL.

In another example, for determining whether an auristatin or resultant antibody-drug conjugate exerts a cytostatic or cytotoxic effect on, for example a HL cell line, cell viability is measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12). Preferred antibody-drug conjugates include those with an $IC_{50}$ value (defined as the mAb concentration that gives 50% cell kill) of less than 1000 ng/ml, preferably less than 500 ng/ml, more preferably less than 100 ng/ml, even most preferably less than 50 or even less than 10 ng/ml on a cell line.

Methods for determining whether a compound binds tubulin are known in the art. See, for example, Muller et al., *Anal. Chem.* 2006, 78, 4390-4397; Hamel et al., *Molecular Pharmacology*, 1995 47: 965-976; and Hamel et al., *The Journal of Biological Chemistry*, 1990 265:28, 17141-17149. For purposes of the present invention, the relative affinity of a compound to tubulin can be determined. Preferred auristatins of the present invention bind tubulin with an affinity ranging from 10 fold lower (weaker affinity) that the binding affinity of MMAE to tubulin to 10 fold, 20 fold or even 100 fold higher (tighter affinity) than the binding affinity of MMAE to tubulin.

Anti-CD30 antibodies suitable for use in accordance with the present compositions and methods include any antibody that specifically binds to the CD30 antigen. Anti-CD30 antibodies are preferably monoclonal and can include, for example, chimeric (e.g., having a human constant region and mouse variable region), humanized, or human antibodies; single chain antibodies; or the like. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments, the antibody is an antigen-binding antibody fragment such as, for example, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, or fragments produced by a Fab expression library, or a CD30-binding fragment of any of the above antibodies. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Typically, the antibodies are human, rodent (e.g., mouse and rat), donkey, sheep, rabbit, goat, guinea pig, camelid, horse, or chicken.

As used herein, "human" antibodies include antibodies having the amino acid sequence of a human immunoglobulin and include antibodies isolated from human immunoglobulin libraries, from human B cells, or from animals transgenic for one or more human immunoglobulin (see, for example in U.S. Pat. Nos. 5,939,598 and 6,111,166).

The antibodies may be monospecific, bispecific, trispecific, or of greater multispecificity (See, e.g., PCT publications WO 93/17715; WO 92/08802; WO 91/00360; and WO 92/05793; Tutt et al., 1991, *J Immunol* 147:60-69; U.S. Pat. Nos. 4,474,893; 4,714,681; 4,925,648; 5,573,920; and 5,601,819; Kostelny et al., 1992, *J Immunol* 148:1547-1553.).

Exemplary anti-CD30 antibodies include, but are not limited to, humanized or chimeric AC10 or HeFi-1 antibodies. Accordingly, an exemplary anti-CD30 antibody comprises one or more CDRs of murine HeFi-1 or murine AC10. In some embodiments, the anti-CD30 antibody comprises one/or one or more variable regions of murine HeFi-1 or murine AC10.

Exemplary anti-CD30 antibodies include functional derivatives or analogs of AC10 and HeFi-1. As used herein, the term "functional" in this context indicates that the functional derivate or analog of AC10 and HeFi-1 is capable of binding to CD30.

In some embodiments, anti-CD30 antibodies not only immunospecifically binds CD30 but also can exert cytostatic and/or cytotoxic effect on malignant cells in, for example HL, wherein the cytostatic or cytotoxic effect is complement-independent and can be achieved in the absence of (i) conjugation to a cytostatic or cytotoxic agent and (ii) effector cells.

The anti-CD30 antibodies may be described or specified in terms of the particular CDRs they comprise. In some embodiments, the antibodies comprise the CDRs of AC10 and/or HeFi-1. In some embodiments, the antibodies are chimeric or humanized forms of AC10 or HeFi-1. The invention encompasses an antibody comprising a heavy or light chain variable domain, said variable domain comprising (a) a set of three CDRs, in which said set of CDRs are from murine monoclonal antibody AC10 or HeFi-1, and (b) a set of four framework regions, in which said set of framework regions differs from the set of framework regions in murine monoclonal antibody AC10 or HeFi-1, respectively, and in which said antibody immunospecifically binds CD30.

Additionally, the antibodies can also be described or specified in terms of their primary structures. Anti-CD30 antibodies having at least 80%, at least 85%, at least 90%, at least 95% and most preferably at least 98% identity (as calculated using methods known in the art and described herein) to the variable regions of murine AC10 or HeFi-1 are also included in the present invention. Antibodies of the present invention may also be described or specified in terms of their binding affinity to CD30. Preferred binding affinities include those with a dissociation constant or Kd less than $5\times10^{-6}$ M, $10^{-6}$ M, $5\times10^{-7}$ M, $10^{-7}$M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times^{-13}$ M, $10^{-13}$ M, $5\times10^{-14}$ M, $10^{-14}$ M, $5\times10^{-15}$ M, or $10^{-15}$ M.

The antibodies also include antibodies that are modified, e.g., by the attachment of any type of molecule to the antibody such that attachment does not prevent the antibody from binding to CD30. For example, but not by way of limitation, the term "antibody" includes antibodies that have been modified, e.g., by glycosylation, deglycosylation, acetylation, pegylation, phosphylation, amidation, derivatization by known protecting/blocking groups, linkage to a cellular ligand or other protein, etc. Any of numerous chemical modifications may be carried out by known techniques, including, but not limited to specific chemical cleavage, acetylation, formylation, metabolic synthesis of tunicamycin, etc.

In some embodiments, the anti-CD30 antibody-drug conjugate is brentuximab vedotin (See e.g., WO04/010957). Brentuximab vedotin is an antibody-drug conjugate (ADC) directed to the CD30 antigen. It comprises an anti-CD30 monoclonal antibody (cAC10) attached by a protease-cleavable linker to a cytotoxic agent, monomethyl auristatin E (MMAE). The ADC employs a linker system that is designed to be stable in the bloodstream but to release MMAE upon internalization into CD30-expressing tumor cells, resulting in target cell death.

In another aspect, therefore, the invention provides a method for inhibiting cellular growth/cellular proliferation comprising contacting a cell with an Aurora kinase inhibitor in combination with an anti-CD30 antibody conjugate, such as, e.g., brentuximab vedotin.

Preferably, the method according to the invention causes an inhibition of cell proliferation of the contacted cells. The phrase "inhibiting cell proliferation" is used to denote an ability of an inhibitor of Aurora kinase and/or anti-CD30 antibody to inhibit cell number or cell growth in contacted cells as compared to cells not contacted with the inhibitor and/or antibody. An assessment of cell proliferation can be made by counting cells using a cell counter or by an assay of cell viability, e.g., a BrdU, MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with an Aurora kinase inhibitor and an anti-CD30 antibody is retarded by at least about 50% as compared to growth of non-contacted cells. In some embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an inhibitor of Aurora kinase and/or an anti-CD30 antibody that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising i) an Aurora kinase inhibitor; and ii) an anti-CD30 antibody.

The present invention provides new combination therapies for the treatment of cancers. In some embodiments, the cancer to be treated by the method of the invention is one in which the activity of an Aurora kinase is amplified and in which the CD30 antigen is expressed. In some embodiments, the cancer is a hematological malignancy. In some embodiments, the hematological malignancy is a lymphoma. Nonlimiting examples of lymphomas include Hodgkin lymphomas, B-cell lymphomas, T-cell lymphomas, natural killer (NK) cell neoplasms and immunodeficiency-associated lymphoproliferative disorders. Nonlimiting examples of Hodgkin lymphomas (HL) include nodular sclerosis HL, mixed cellularity HL, lymphocyte-rich HL, and lymphocyte depleted or not depleted HL. Nonlimiting examples of lymphomas other than Hodgkin lymphomas include, for example, low grade/follicular non-Hodgkin's lymphoma (NHL), follicular non-Hodgkin's lymphoma (NHL), small lymphocytic (SL) NHL, T or B prolymphocytic leukemia, diffuse large B cell lymphoma (DLBCL), peripheral T cell lymphomas (PTCL), PTCL-not otherwise specified (PTCL-NOS), mantle cell lymphoma, marginal zone lymphomas, mature T-cell lymphoma, B or T cell lymphoblastic lymphoma, Burkitt's lymphoma, primary thyroid lymphoma, Waldenstrom's Macroglobulinemia, lymphoplasmacytic lymphoma, mycosis fungoides, adult T-cell leukemia/lymphoma (ATLL), angioimmunoblastic lymphoma (AITL), enteropathy-associated T-cell lymphoma (EATL), and anaplastic large cell lymphoma (ALCL). It should be clear to those of skill in the art that these pathological conditions may often have different names due to differing/changing classification systems.

In some embodiments the lymphoma is Hodgkin lymphoma. In some embodiments, the lymphoma is diffuse large B-cell lymphoma. In some embodiments, the lymphoma is anaplastic large cell lymphoma. In some embodiments, the lymphoma is peripheral T-cell lymphoma. In some embodiments, the lymphoma is classified as being CD30-negative. In some embodiments, the lymphoma is classified as being CD30-positive. In some embodiments the lymphoma is CD30-positive Hodgkin lymphoma. In some embodiments, the lymphoma is CD30 positive diffuse large B-cell lymphoma. In some embodiments, the lymphoma is CD30-positive anaplastic large cell lymphoma. In some embodiments, the lymphoma is CD30-positive peripheral T-cell lymphoma.

In some embodiments, the cancer is a solid tumor. Non-limiting examples of solid tumors include ovarian cancer (e.g., ovarian epithelial carcinoma or ovarian serous carcinoma), skin cancer (e.g., melanoma and/or skin squamous cell carcinoma), breast cancer (e.g., triple negative breast cancer), thyroid cancer (e.g., anaplastic thyroid carcinoma), pancreatic cancer (e.g., undifferentiated pancreatic carcinoma or adenocarcinoma), lung cancer (e.g., small cell or squamous cell lung cancer), thymus cancer (e.g., thymic carcinoma), anal cancer (e.g., anal squamous cell carcinoma), endometrial cancer, uterine cancer, gynecologic carcinosarcomas, urethral cancer, genitourinary squamous cell carcinomas, carcinoma of unknown primary, Sertoli cell tumors, and leydig cell tumors. The solid tumor can be a primary or metastatic tumor.

In some embodiments, the invention provides for an antibody-drug conjugate for use in a method of treating cancer (e.g., the hematological malignancies or solid tumors described herein), by administration simultaneously, separately, consecutively or sequentially with an Aurora A kinase inhibitor. In some embodiments, the present invention provides for an Aurora kinase A inhibitor for use in a method for treating cancer (e.g., the hematological malignancies or solid tumors described herein), by administration simultaneously, separately, consecutively or sequentially with an antibody-drug conjugate.

In some embodiments, the present invention provides for an antibody-drug conjugate for use in the manufacture of a medicament for treating cancer (e.g., the hematological malignancies or solid tumors described herein), wherein the antibody-drug conjugate is administered simultaneously, separately, consecutively or sequentially with an Aurora A kinase inhibitor. In some embodiments, the present invention provides for an Aurora A kinase inhibitor for use in the manufacture of a medicament for treating cancer (e.g., the hematological malignancies or solid tumors described herein), wherein the Aurora A kinase inhibitor is administered simultaneously, separately, consecutively or sequentially with an antibody-drug conjugate.

The antibody-drug conjugate and Aurora A kinase inhibitor are administered in such a way that they provide a combination benefit in the treatment of lymphomas in a patient. For example, the combined administration of the antibody-drug conjugate and Aurora A kinase inhibitor provides a synergistic effect in the treatment of lymphomas in a patient. Administration can be by any suitable means provided that the administration provides the desired therapeutic effect, e.g., synergism or other combination benefit. In some embodiments, the antibody-drug conjugate compound and Aurora A kinase inhibitor are administered during the same cycle of therapy, e.g., during one cycle of therapy, e.g., a three or four week time period, both the antibody-drug conjugate compound and the specified chemotherapeutic drug(s) are administered to the subject. In some embodiments of the present invention, administration of the antibody-drug conjugate compound will be at such a time that it sensitizes cancerous cells to treatment with an Aurora A kinase inhibitor, i.e., sequentially, e.g., immediately prior to chemotherapeutic treatment, e.g., less than 2 hours prior to chemotherapeutic treatment.

In some embodiments, the antibody-drug conjugate and Aurora A kinase inhibitor are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In some embodiments, the treatment period during which an agent is administered is then followed by a non-treatment period of particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

The dosage of the antibody-drug conjugate compound administered to a patient will also depend on frequency of administration. The present invention contemplates antibody-drug conjugate compound delivery once during the treatment cycle or by a split delivery.

The present invention encompasses embodiments wherein the antibody-drug conjugate compound will be administered in a dose range of 0.1 mg/kg to 2.7 mg/kg of the subject's body weight per dose, 0.5 mg/kg to 2.0 mg/kg of the subject's body weight per dose, 1.0 mg/kg to 2.0 mg/kg of the subject's body weight per dose, and 1.0 mg/kg to 1.8 mg/kg of the subject's body weight per dose. Other ranges are encompassed by the present invention as long as they produce the desired result. In one embodiment, the antibody-drug conjugate compound will be administered at a dose of about 1.2 mg/kg of the subject's body weight per dose. In another embodiment, the antibody-drug conjugate compound will be administered at a dose of about 1.8 mg/kg of the subject's body weight per dose.

The present invention encompasses treatment schedules wherein the total dosage of the antibody-drug conjugate compound, administered to a patient will be, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over a treatment cycle, e.g., a 3 or 4 week time period. In some embodiments, the total dosage of the antibody-drug conjugate compound administered to a patient will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.0 mg/kg to about 3.0 mg/kg over a treatment cycle, e.g., a 3 or 4 week time period. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle, e.g., a 3 or 4 week time period. In some embodiments, the total dosage of the antibody-drug conjugate compound, administered to a patient will be 1.8 mg/kg of the subject's body weight over a treatment cycle, e.g., a 3 or 4 week time period. In some embodiments, the total dosage of the antibody-drug conjugate compound, administered to a patient will be 2.4 mg/kg of the subject's body weight over a treatment cycle, e.g., a 3 or 4 week time period. In some embodiments, the total dosage of the antibody-drug conjugate compound, administered to a patient will be, 3.6 mg/kg of the subject's body weight over a treatment cycle, e.g., a 3 or 4 week time period. In some embodiments, the antibody-drug conjugate compound will be administered at a dose of 1.2 mg/kg of the subject's body weight over a treatment cycle, e.g., a 3 or 4 week time period. In some embodiments, the antibody-drug conjugate compound will be administered at a dose of 1.8 mg/kg of the subject's body weight over a treatment cycle, e.g., a 3 or 4 week time period.

The present invention contemplates administration of the drug for one or more treatment cycles, for example, 1, 2, 3, 4, 5, 6, or more, treatment cycles. In some embodiments, there will be periods of rest between one or more of the treatment cycles. For example, in some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the antibody-drug conjugate compound once during a treatment schedule, e.g., on day 1 of a 21 day cycle, twice during a treatment cycle, e.g., on days 1 and 15 of a 21 day cycle or on days 1 and 15 of a 28 day cycle, and three times during a treatment cycle, e.g., on days 1, 8 and 15 of a 21 day cycle or on days 1, 8 and 15 of a 28 day cycle. Other dosage schedules are encompassed by the present invention.

The present invention encompasses treatment schedules wherein the antibody-drug conjugate compound is administered once during a treatment cycle, e.g., a 3 or 4 week time period. For example, in some embodiments, the antibody-drug conjugate will be administered on the third week of a 3 or 4 week treatment cycle, e.g., on day 21 of a three or four week cycle. In some embodiments, the antibody-drug conjugate will be administered on day 1 of a 3 or 4 week treatment cycle, or on any other day of a three or four week treatment cycle.

In other embodiments the antibody-drug conjugate compound will be administered more than once during a treatment cycle. For example, in some embodiments, the antibody-drug conjugate compound will be administered weekly for three consecutive weeks in a three or four week treatment cycle. For example, in some embodiments, the antibody-drug conjugate compound will be administered on days 1, 8 and 15 of each 21 day treatment cycle. In some embodiments, the antibody-drug conjugate compound will be administered on days 1, 8, and 15 of each 28 day treatment cycle.

In even other embodiments the antibody-drug conjugate compound will be administered every two weeks in a four week treatment cycle. For example, in some embodiments, the antibody-drug conjugate compound will be administered on days 1 and 15 of each 28 day treatment cycle.

In any of the above-listed embodiments, the dosage of the antibody-drug conjugate compound administered to a patient can be, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over the treatment cycle. In some embodiments, the total dosage of the antibody-drug conjugate compound administered to a patient will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.5 mg/kg to about 3 mg/kg over the treatment cycle. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle. In some embodiments, the dosage of the antibody-drug conjugate compound will generally be 0.1 mg/kg to 5 mg/kg of the subject's body weight, 0.1 mg/kg to 3.2 mg/kg of the subject's body weight, more typically 0.1 mg/kg to 2.7 mg/kg, even more typically 0.2 mg/kg to 1.8 mg/kg, 0.2 mg/kg to 1.2 mg/kg, 0.2 mg/kg to 1.5 mg/kg, 1 mg/kg to 1.5 mg/kg, or 0.5 to 1.2 mg/kg, of the subject's body weight on days 1 and 15 of each 28 day cycle. In some embodiments, the dosage will be about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, or about 1.8 mg/kg of the subject's body weight on days 1 and 15 of each 28 day cycle.

It will be readily apparent to those skilled in the art that other antibody-drug conjugate compound doses or frequencies of administration that provide the desired therapeutic effect are suitable for use in the present invention.

The therapeutically effective amounts or suitable dosages of the selective inhibitor of Aurora A kinase depends upon a number of factors, including the nature of the severity of the condition to be treated, the particular inhibitor, the route of administration and the age, weight, general health, and response of the individual patient. In some embodiments, the suitable dose level is one that achieves an effective exposure as measured by increased skin mitotic index, or decreased chromosome alignment and spindle bipolarity in tumor mitotic cells, or other standard measures of effective exposure in cancer patients. In some embodiments, the suitable dose level is one that achieves a therapeutic response as measured by tumor regression, or other standard measures of disease progression, progression free survival or overall survival. In some embodiments, the suitable dose level is one that achieves this therapeutic response and also minimizes any side effects associated with the administration of the therapeutic agent.

Suitable daily dosages of selective inhibitors of Aurora A kinase can generally range, in single or divided or multiple doses, from about 10% to about 100% of the maximum tolerated dose as a single agent. In some embodiments, the suitable dosages are from about 15% to about 100% of the maximum tolerated dose as a single agent. In some embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In some embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, or about 110% of the maximum tolerated dose as a single agent.

It will be understood that a suitable dosage of a selective inhibitor of Aurora A kinase may be taken at any time of the day or night. In some embodiments, a suitable dosage of a selective inhibitor of Aurora A kinase is taken in the morning. In some other embodiments, a suitable dosage of a selective inhibitor of Aurora A kinase is taken in the evening. In some other embodiments, a suitable dosage of a selective inhibitor of Aurora A kinase is taken both in the morning and the evening. It will be understood that a suitable dosage of a selective inhibitor of Aurora A kinase may be taken with or without food. In some embodiments a suitable dosage of a selective inhibitor of Aurora A kinase is taken with a meal. In some embodiments a suitable dosage of a selective inhibitor of Aurora A kinase is taken while fasting.

Suitable daily dosages of alisertib can generally range, in single or divided or multiple doses, from about 20 mg to about 120 mg per day. Other suitable daily dosages of alisertib can generally range, in single or divided or multiple doses, from about 30 mg to about 90 mg per day. Other suitable daily dosages of alisertib can generally range, in single or divided or multiple doses, from about 40 mg to about 80 mg per day. In some embodiments, the suitable dosages are from about 10 mg twice daily to about 50 mg twice daily. In some other embodiments, the suitable dosages are from about 15 mg twice daily to about 45 mg twice daily. In some other embodiments, the suitable dosages are from about 20 mg twice daily to about 40 mg twice daily. In some other embodiments, the suitable dosages are from about 25 mg twice daily to about 40 mg twice daily. In some embodiments, suitable dosages are about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, or about 120 mg per day. In certain other embodiments, suitable dosages are about 10 mg, about 15 mg, about 20 mg, about 25 mg, about 30 mg, about 35 mg, about 40 mg, about 45 mg, about 50 mg, about 55 mg, or about 60 mg twice daily. In some embodiments, the suitable dosage of alisertib is about 30 mg twice daily. In some embodiments, the suitable dosage of alisertib is about 35 mg twice daily. In some embodiments, the suitable dosage of alisertib is about 40 mg twice daily. In some embodiments, the suitable dosage of alisertib is about 50 mg twice daily.

In some embodiments, a first treatment period in which a first amount of the selective inhibitor of Aurora A kinase is administered can be followed by another treatment period in which a same or different amount of the same or a different selective inhibitor of Aurora A kinase is administered. The second treatment period can be followed by other treatment periods. During the treatment and non-treatment periods, one or more additional therapeutic agents can be administered to the patient.

In some embodiments, the administration is on a 21-day schedule in which the Aurora A kinase inhibitor is administered on days 1, 2, 3, 4, 5, 6, and 7 of a 21-day schedule. In some embodiments, the administration is on a 21-day schedule in which alisertib or a pharmaceutically acceptable salt is administered on days 1, 2, 3, 4, 5, 6, and 7 of a 21 day schedule. In some embodiments, the administration is on a 21-day schedule in which alisertib or a pharmaceutically acceptable salt is administered twice-daily on days 1, 2, 3, 4, 5, 6, and 7 of a 21 day schedule.

Administration of the antibody-drug conjugate compound and the Aurora A kinase inhibitor can be on the same or different days provided that administration provides the desired therapeutic effect. In some embodiments of the present invention, administration of the antibody-drug conjugate compound and the Aurora A kinase inhibitor will be on the same days. In some embodiments of the present invention, administration of the antibody-drug conjugate compound and the Aurora A kinase inhibitor will be on the same and/or different days, e.g., the antibody-drug conjugate will be administered on day 1 of a 21 day cycle and the Aurora A kinase inhibitor will be administered on days 1-7 of the 21 day cycle. In some embodiments, the antibody-drug conjugate compound and the Aurora A kinase inhibitor will be administered on the same days and the Aurora A kinase inhibitor will be administered following completion of administration of the antibody-drug conjugate, e.g., the Aurora A kinase inhibitor will be administered less than 2 hours following administration of the antibody-drug conjugate, e.g., 30 minutes following administration of the antibody-drug conjugate. Alternative treatment schedules are encompassed by the present invention as long as they produce the desired result. The Aurora A kinase inhibitor may be administered with the antibody-drug conjugate in a single dosage form or as a separate dosage form. When administered as a separate dosage form, the anti-antibody-drug conjugate may be administered prior to, at the same time as, or following administration of the Aurora A kinase inhibitor of the invention.

In some embodiments, administration of alisertib or a pharmaceutically acceptable salt is twice daily on days 1, 2, 3, 4, 5, 6, and 7 of a 21-day cycle and brentuximab vedotin is administered on day 1 of the 21-day cycle.

In some embodiments, administration of synergistic amount of the therapeutic agents encompasses administering brentuximab vedotin once on day 1 during the treatment cycle of 21 days in an amount of about 0.8 mg/kg to about 2.0 mg/kg, about 1.2 mg/kg to about 2.7 mg/kg, or about 1.2 mg/kg to about 2 mg/kg of the subject's body weight in combination with administering alisertib or a pharmaceutically acceptable salt thereof on days 1, 2, 3, 4, 5, 6, and 7 during the treatment cycle of 21 days in amount of about 10 mg, about 15 mg, about 20 mg, about 25 mg, about 30 mg, about 35 mg, about 40 mg, about 45 mg, about 50 mg, about 55 mg, or about 60 mg twice daily (measured as the amount of alisertib).

In some embodiments, administration of a synergistic amount of the therapeutic agents encompasses administering brentuximab vedotin once on day 1 during the treatment cycle of 21 days in an amount of about 1.8 mg/kg of the subject's body weight in combination with administering alisertib or a pharmaceutically acceptable salt thereof on days 1, 2, 3, 4, 5, 6, and 7 during the treatment cycle of 21 days in amount of about 50 mg twice daily (measured as the amount of alisertib).

In some embodiments, administration of alisertib or a pharmaceutically acceptable salt is twice daily on days 1-3 and 8-10 of a 21-day cycle and brentuximab vedotin is administered on day 1 of the 21-day cycle.

In some embodiments, administration of synergistic amount of the therapeutic agents encompasses administering brentuximab vedotin once on day 1 during the treatment cycle of 21 days in an amount of about 0.8 mg/kg to about 2.0 mg/kg, about 1.2 mg/kg to about 2.7 mg/kg, or about 1.2 mg/kg to about 2 mg/kg of the subject's body weight in combination with administering alisertib or a pharmaceutically acceptable salt thereof on days 1-3 and 8-10 during the treatment cycle of 21 days in amount of about 10 mg, about 15 mg, about 20 mg, about 25 mg, about 30 mg, about 35 mg, about 40 mg, about 45 mg, about 50 mg, about 55 mg, or about 60 mg twice daily (measured as the amount of alisertib).

In some embodiments, administration of a synergistic amount of the therapeutic agents encompasses administering brentuximab vedotin once on day 1 during the treatment cycle of 21 days in an amount of about 1.8 mg/kg of the subject's body weight in combination with administering alisertib or a pharmaceutically acceptable salt thereof on days 1-8 and 8-10 during the treatment cycle of 21 days in amount of about 50 mg twice daily (measured as the amount of alisertib).

In some embodiments, administration of alisertib or a pharmaceutically acceptable salt is twice daily on days 1-3 and 8-10 and 15-17 of a 28-day cycle and brentuximab vedotin is administered on day 1 of a 28-day cycle.

In some embodiments, administration of synergistic amount of the therapeutic agents encompasses administering brentuximab vedotin once on day 1 during a treatment cycle of 28 days in an amount of about 0.8 mg/kg to about 2.0 mg/kg, about 1.2 mg/kg to about 2.7 mg/kg, or about 1.2 mg/kg to about 2 mg/kg of the subject's body weight in combination with administering alisertib or a pharmaceutically acceptable salt thereof on days 1-3, 8-10 and 15-17 during a treatment cycle of 28 days in amount of about 10 mg, about 15 mg, about 20 mg, about 25 mg, about 30 mg, about 35 mg, about 40 mg, about 45 mg, about 50 mg, about 55 mg, or about 60 mg twice daily (measured as the amount of alisertib).

In some embodiments, administration of a synergistic amount of the therapeutic agents encompasses administering brentuximab vedotin once on day 1 during a treatment cycle of 28 days in an amount of about 1.8 mg/kg of the subject's body weight in combination with administering alisertib or a pharmaceutically acceptable salt thereof on days 1-8, 8-10, and 15-17 during a treatment cycle of 28 days in amount of about 50 mg twice daily (measured as the amount of alisertib).

In some embodiments, the method to treat a patient suffering from Hodgkin lymphoma comprises administering to said patient a therapeutically effective amount of alisertib or a pharmaceutically acceptable salt thereof, separately with, simultaneously with, sequentially with, or consecutively with (e.g., before or after) brentuximab vedotin. In some embodiments, the method to treat a patient suffering from CD30-positive Hodgkin lymphoma comprises administering to said patient a therapeutically effective amount of alisertib or a pharmaceutically acceptable salt thereof, separately with, simultaneously with, sequentially with, or consecutively with (e.g., before or after) brentuximab vedotin.

In some embodiments, the method to treat a patient suffering from diffuse large B-cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin. In some embodiments, the method to treat a patient suffering from CD30-positive diffuse large B-cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin.

In some embodiments, the method to treat a patient suffering from anaplastic large cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin. In some embodiments, the method to treat a patient suffering from CD30-positive anaplastic large cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin.

In some embodiments, the method to treat a patient suffering from peripheral T-cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin. In some embodiments, the method to treat a patient suffering from CD30-positive peripheral T-cell lymphoma comprises administering to said patient a therapeutically effective amount of alisertib or a pharmaceutically acceptable salt thereof, separately with, simultaneously with, sequentially with, or consecutively with (e.g., before or after) brentuximab vedotin.

The selective inhibitor of Aurora A kinase can be administered by any method known to one skilled in the art. For example, the selective inhibitor of Aurora A kinase can be administered in the form of a composition, in some embodiments a pharmaceutical composition of the selective inhibitor of Aurora A kinase and a pharmaceutically acceptable carrier, such as those described herein. Preferably, the pharmaceutical composition is suitable for oral administration. In some embodiments, the pharmaceutical composition is a tablet for oral administration, such as an enteric coated tablet. Such tablets are described in US Publication No. 2010/0310651, which is hereby incorporated by reference in its entirety. In some other embodiments, the pharmaceutical composition is a liquid dosage form for oral administration. Such liquid dosage forms are described in US Publication No. 2011/0039826, hereby incorporated by reference. In some embodiments, these compositions optionally further comprise one or more additional therapeutic agents.

The antibody-drug conjugate can be administered by any method known to one skilled in the art. For example, the antibody-drug conjugate can be administered in the form of a composition, in some embodiments a pharmaceutical composition of an antibody-drug conjugate and a pharmaceutically acceptable carrier, such as those described herein. In some embodiments, the pharmaceutical composition is a lyophilized powder, which when reconstituted, can be administered via an intravenous route, such as intravenous injection or intravenous infusion. In some embodiments, the antibody-drug conjugate is administered via intravenous injection. In some embodiments, the antibody-drug conjugate is administered via intravenous infusion. In another embodiment brentuximab vedotin is administered via intravenous infusion.

If a pharmaceutically acceptable salt of the Aurora kinase inhibitor is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy,* 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

In some embodiments, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

Compositions for use in the method of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

EXAMPLES

Definitions
ANOVA Analysis of variance
ΔAUC difference in the area under the curve
BID twice daily
IV intravenous(ly)
MTD maximum tolerated dose
SCID severe combined immunodeficiency
po. Orally (by mouth, per os)
QD once daily
QW or Q7D once weekly
SC subcutaneous(ly)
TG treatment group
TGI tumor growth inhibition
In Vivo Tumor Efficacy Model SR-786 ($4.0 \times 10^6$) tumor cells in RPMI-1640 media were aseptically injected into the subcutaneous space in the right dorsal flank of CB17 SCID female mice (Taconic Farms, Inc) using a 26 G 5/8 needle.
Test Agents Brentuximab vedotin (SGN35), one vial (Seattle Genetics) was reconstituted in 10.5 ml sterile water to give a stock solution at 4.76 mg/ml concentration. The stock solution was formulated in 0.9% saline to reach the desired concentration and administered by intraperitoneal injection (IP) q4Dx21 days at 0.3 mg/kg and 0.4 mg/kg.

MLN8237 was formulated in 10% hydroxypropyl-beta-cyclodextrin and 1% sodium bicarbonate (10% HPbCD+1% NaHCO$_3$) and administered by oral injection (1 cc syringe, 20-22 gauge) on QD schedule at 10 mg/kg and 20 mg/kg for 21 days. MLN8237 as used in the experimental section refers to alisertib sodium salt and the amount referenced is the amount of alisertib used.
Tumor Measurements:

Tumors were measured twice weekly using a vernier caliper. Tumor volumes were calculated using standard procedures (0.5×(length×width)). When the tumors reached a volume of approximately 200 mm$^3$ (SR-786), mice were randomized into 6-8 groups as described in the tables below, and injected with vehicle, MLN8237 or SGN35 or the combination of MLN8237 with SGN35, at various doses as described below in Tables 1 and 2. Tumor size and body weight were measured approximately twice a week for the duration of the study. Mice were euthanized when their tumor volume reached 10% of their body weight, or when the average tumor volume of a treatment or control group reached approximately 2000 mm$^3$. Tumor growth continued to be monitored after the dosing period in this study. Tumor volume on study day 15 for all groups is shown in Table 1. Tumor volume on study day 21 for all groups is shown in Table 2. Average tumor volume is reported as a function of time for selected groups in FIG. 1A and FIG. 1B.

Statistical Analyses of Combination Effect for Tumor Growth in Subcutaneous Xenograft Models.

The synergy analysis is based on the tumor volume data from day 0 to 21. Volume measurements below 25 cubic mm are excluded from the analysis because very low volumes cannot be measured accurately. The remaining measurements are log transformed and fit to a simple linear model with the measurement day as a covariate. The data are fit separately for the different animals to yield an estimated tumor growth rate for each animal in each treatment group. Based on the growth rates, the synergy score for the combination of agents A and B is defined as $$100*(\text{mean}(\mu_{AB})-\text{mean}(\mu_A)-\text{mean}(\mu_B)+\text{mean}(\mu_{ctl}))/\text{mean}(\mu_{ctl}):$$

where $\mu_{AB}$, $\mu_A$, $\mu_B$, and $\mu_{ctl}$ are the mean tumor growth rates for animals in the combination group, the A group, the B group, and the control group, respectively. The standard error of the synergy score is computed based on the variation in the growth rates among the animals. A two sided t-test is used to determine if the synergy score is significantly different from zero. If the P-value is above 0.05, then the combination is considered to be additive. If the P-value is below 0.05, and the synergy score is less than zero, then the combination is considered to be synergistic. If the P-value is below 0.05, the synergy score is greater than zero, and the combination is more effective than either agent alone, then the combination is considered to be subadditive. Otherwise, the combination is classified as antagonistic.

Results

A mouse xenograft model, performed as described in the method above, was used to assess the combination effect in vivo of MLN8237 and SGN35. The detail for this study is as shown below in Tables 1 and 2. The results were analyzed using the statistical analysis described above and the classification of the combination is shown below in Table 3. Alisertib sodium salt was used in all experiments; the values listed in Tables 1 and 2 reflect the amounts of alisertib used.

In the SR786 xenograft model (shown in FIG. 1A), dosing of the single agents (MLN8237 P.O 10 mg/kg and 20 mg/kg QD) and SGN35 (0.3 and 0.4 mg/kg I.P Q4d) inhibited tumor growth compared to the control vehicle group. Tumors in the single agent groups continued to grow in size during the treatment period. The combination treatment using the same doses and schedules generated synergistic or additive anti tumor activity and led to complete inhibition of tumor growth with a decrease in tumor volume compared to the starting volume. 7/7 mice were shown to be tumor free on days 15 and 21 post treatment in the MLN8237 10 mg/kg combination with SGN35 0.4 mg/kg group (Group 8). 7/7 mice were shown to be tumor free on day 29 post treatment (dosing with MLN8237 was stopped on day 21) in MLN8237 10 mg/kg combination with SGN35 0.3 mg/kg group (Group 6). All treatment groups from the study are shown in Tables 1 and 2. In all arms of the study the doses are well tolerated. Duration of response was evaluated by continuing to measure tumor re-growth up to 124 days. No tumors were found in any mice in the combination groups MLN8237 10 mg/kg with SGN35 at 0.3 mg/kg and 0.4 mg/kg as shown in FIG. 1B (Groups 6 and 8).

TABLE 1

Combination of MLN8237 and SGN35 in SR786 xenograft model (15 days)

| Group | Treatment | Dosing Regimen | Route | average tumor volume day 15 | SEM tumor volume day 15 | number of mice in group (number on Day 15) |
|---|---|---|---|---|---|---|
| 1 | 0.9% Saline 10% HPbCD + 1% NaHCO3 | QD, IP/Q4d | I.P, P.O | 1947.1 | 360.2 | 7 |
| 2 | 0.3 mg/kg SGN35 | Q4d | I.P | 1136.1 | 288.5 | 7 |
| 3 | 0.4 mg/kg SGN35 | Q4d | I.P | 491.3 | 238.8 | 7 |
| 4 | 10 mg/kg MLN8237 | QD | P.O | 625.4 | 232.5 | 7 |
| 5 | 20 mg/kg MLN8237 | QD | P.O | 387.1 | 154.7 | 7 |
| 6 | 0.3 mg/kg SGN35; 10 mg/kg MLN8237 | Q4d, QD | I.P; P.O | 102.3 | 47 | 7 |
| 7 | 0.3 mg/kg SGN35; 20 mg/kg MLN8237 | Q4d; QD | I.P; P.O | 153.4 | 68.1 | 7 |
| 8 | 0.4 mg/kg SGN35; 10 mg/kg MLN8237 | Q4d; QD | I.P; P.O | 0 | 0 | 7 |

TABLE 2

Combination of MLN8237 and SGN35 in SR786 xenograft model (21 days)

| Group | Treatment | Dosing Regimen | Route | average tumor volume day 21 | SEM tumor volume day 21 | number of mice in group (number on Day 21) |
|---|---|---|---|---|---|---|
| 1 | 0.9% Saline 10% HPbCD + 1% NaHCO3 | QD, IP/Q4d | I.P, P.O | | | 0 |
| 2 | 0.3 mg/kg SGN35 | Q4d | I.P | 1676 | 446 | 7 |
| 3 | 0.4 mg/kg SGN35 | Q4d | I.P | 553.8 | 264.7 | 7 |
| 4 | 10 mg/kg MLN8237 | QD | P.O | 1121 | 453.6 | 7 |
| 5 | 20 mg/kg MLN8237 | QD | P.O | 576.4 | 253.5 | 7 |
| 6 | 0.3 mg/kg SGN35; 10 mg/kg MLN8237 | Q4d, QD | I.P; P.O | 25.9 | 14.2 | 7 |
| 7 | 0.3 mg/kg SGN35; 20 mg/kg MLN8237 | Q4d; QD | I.P; P.O | 134.1 | 65.9 | 7 |
| 8 | 0.4 mg/kg SGN35; 10 mg/kg MLN8237 | Q4d; QD | I.P; P.O | 0 | 0 | 7 |

TABLE 3

Classification for in vivo combination of MLN8237 and SGN35 in SR786 xenograft model

| Treatment groups | Synergy score day21 | Synergy score SEM | P-Value | Combination Outcome |
|---|---|---|---|---|
| SGN35 0.3 mg/kg + MLN8237 10 mg/kg | −69.6 | 23.2 | 0.008 | Synergy |
| SGN35 0.3 mg/kg + MLN8237 20 mg/kg | −0.4 | 30.6 | 0.990 | Additivity |
| SGN35 0.4 mg/kg + MLN8237 10 mg/kg | −76.0 | 37.2 | 0.059 | Additivity |

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A method of treating a patient suffering from a lymphoma, comprising administering to the subject a therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof simultaneously with or consecutively with a therapeutically effective amount of brentuximab vedotin,
wherein the 4-{[9-chloro-7-(2-fluoro-6-methoxyphenyl)-5H-pyrimido[5,4-d][2]benzazepin-2-yl]amino}-2-methoxybenzoic acid or pharmaceutically acceptable salt thereof is administered on each of days 1-3 and 8-10 of a 21-day cycle, or each of days 1-3, 8-10, and 15-17 of a 28-day cycle; and wherein the brentuximab vedotin is administered on day 1 of a 21-day cycle.

2. The method of claim 1, wherein the lymphoma is selected from the group consisting of: Hodgkin lymphoma, peripheral T-cell lymphoma (PTCL), diffuse large B-cell lymphoma (DLBCL), and anaplastic large cell lymphoma (ALCL).

3. The method of claim 1, wherein the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 10 mg to about 50 mg given in two divided doses on the day of administration.

4. The method of claim 1, wherein the therapeutically effective amount of brentuximab vedotin is about 1.0 mg/kg to 2.0 mg/kg of the patient's body weight per dose.

5. The method of claim 3, wherein the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 30 mg given in two divided doses on the day of administration.

6. A method of treating a patient suffering from a lymphoma, comprising administering to the subject a therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof simultaneously with or consecutively with a therapeutically effective amount of brentuximab vedotin,
wherein the 4-{[9-chloro-7-(2-fluoro-6-methoxyphenyl)-5H-pyrimido[5,4-d][2]benzazepin-2-yl]amino}-2-methoxybenzoic acid or pharmaceutically acceptable salt thereof is administered on each of days 1-3 and 8-10 of a 21-day cycle, or each of days 1-3, 8-10, and 15-17 of a 28-day cycle.

7. The method of claim 6, wherein the brentuximab vedotin is administered on day 1 of a 21-day cycle; and wherein the therapeutically effective amount of brentuximab vedotin is about 1.0 mg/kg to 2.0 mg/kg of the patient's body weight per dose.

8. The method of claim 6, wherein the lymphoma is selected from the group consisting of: Hodgkin lymphoma, peripheral T-cell lymphoma (PTCL), diffuse large B-cell lymphoma (DLBCL), and anaplastic large cell lymphoma (ALCL).

9. The method of claim 6, wherein the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 10 mg to about 50 mg given in two divided doses on the day of administration.

10. The method of claim 9, wherein the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 30 mg given in two divided doses on the day of administration.

11. The method of claim 6, wherein the therapeutically effective amount of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is about 10 mg to about 50 mg.

* * * * *